(12) United States Patent
Berg et al.

(10) Patent No.: US 7,342,022 B2
(45) Date of Patent: Mar. 11, 2008

(54) COMPOUNDS IN THE TREATMENT OF DEMENTIA RELATED DISEASES, ALZHEIMER'S DISEASE AND CONDITIONS ASSOCIATED WITH GLYCOGEN SYNTHASE KINASE-3

(75) Inventors: Stefan Berg, Södertälje (SE); Ratan Bhat, Södertälje (SE); Philip Edwards, Wilmington, DE (US); Sven Hellberg, Södertälje (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/499,388

(22) PCT Filed: Dec. 18, 2002

(86) PCT No.: PCT/SE02/02371

§ 371 (c)(1),
(2), (4) Date: Jun. 17, 2004

(87) PCT Pub. No.: WO03/055877

PCT Pub. Date: Jul. 10, 2003

(65) Prior Publication Data

US 2005/0222181 A1    Oct. 6, 2005

Related U.S. Application Data

(60) Provisional application No. 60/344,885, filed on Dec. 21, 2001.

(51) Int. Cl.

| | |
|---|---|
| A61K 31/55 | (2006.01) |
| A61K 31/517 | (2006.01) |
| C07D 401/14 | (2006.01) |
| C07D 403/04 | (2006.01) |
| C07D 403/14 | (2006.01) |
| A61P 3/08 | (2006.01) |
| A61P 25/28 | (2006.01) |
| C07D 209/34 | (2006.01) |

(52) U.S. Cl. .............................. 514/266.2; 514/212.08; 544/284; 540/524

(58) Field of Classification Search ............. 514/266.2, 514/217.06, 217.02, 212.08; 540/567, 524; 544/284
See application file for complete search history.

(56) References Cited

U.S. PATENT DOCUMENTS

| 6,265,411 B1 * | 7/2001 | Thomas et al. .......... 514/266.2 |
| 6,294,532 B1 * | 9/2001 | Thomas et al. .......... 514/228.2 |
| 7,205,314 B2 | 4/2007 | Berg et al. |
| 2005/0070559 A1 | 3/2005 | Berg et al. |
| 2005/0075351 A1 | 4/2005 | Berg et al. |

FOREIGN PATENT DOCUMENTS

| EP | 1136493 A1 | 9/2001 |
| WO | WO-95/33750 A1 | 12/1995 |
| WO | WO-97/42187 A1 | 11/1997 |
| WO | WO-99/10349 A1 | 3/1999 |
| WO | WO-00/10975 A1 | 3/2000 |

OTHER PUBLICATIONS

Piyasena Hewawasam et al., "Synthesis and Structure-Activity Relationships of 3-Arylosindoles: A new Class of Calcium-Dependent, Large Conductance Potassium (Maxi-K) Channel Openers with Neuroprotective Properties". J. Med. Chem., vol. 45, 2002, pp. 1487-1499.

Imahori and Uchida., Physiology and Pathology of Tau Protein Kinases in Relation to Alzheimer'Disease. J. Biochem 121, 1997, pp. 179-188.

Hoshi et al., "Regulation of mitochondrial pyruvate dehydrogenase activity by tau protein kinase I/glycogen synthase kinase 3β in brain", PNAS vol. 93, Apr. 1996, pp. 2719-2723.

Bhat et al., "Regulation and localization of tyrosine$^{216}$ phosphorylation of glycogen synthase kinase-3β in cellular and animal models of neuronal degeneration", PNAS vol. 97, No. 20, Sep. 2000, pp. 11074-11079.

Stambolic et al., "Lithium inhibits glycogen synthase kinase-3 activity and mimics wingless signalling in intact cells", Current Biol. 1996, vol. 6, pp. 1664-1668.

Klein and Melton, "A molecular mechanism for the effect of lithium on development", Proc. Natl. Acad. Sci. USA, vol. 93, Aug. 1996, pp. 8455-8459.

Kozlovsky et al., "Low GSK-3β Immunoreactivity in Postmortem Frontal Cortex of Schizophrenic Patients", Am. J. Psychiatry, May 2000, vol. 157(5), pp. 831-833.

(Continued)

Primary Examiner—Emily Bernhardt
Assistant Examiner—Tamthom N. Truong

(57) ABSTRACT

The present invention relates to new compounds of formula I wherein $R^1$, $R^2$, $R^3$, n, m are defined as in claim 1, a process for their preparation and new intermediates used in the preparation thereof, pharmaceutical formulations containing said therapeutically active compounds and to the use of said active compounds in therapy, especially in the prevention and/or treatment of dementia related diseases, Alzheimer's Disease and conditions associated with glycogen synthase kinase-3

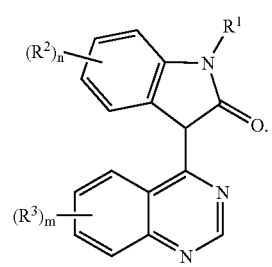

1 Claim, No Drawings

OTHER PUBLICATIONS

Cotter et al., Abnormalities of Wnt signalling in schizophrenia-evidence for neurodevelopmental abnormality, NeuroReport, vol. 9, May 1998, pp. 1379-1383.

Nikoulina et al., "Potential role of glycogen synthase kinase-3 in skeletal muscle insulin resistance if type 2 diabetes", Diabetes, vol. 49, Feb. 2000, pp. 263-271.

Gat et al., "De Novo Hair Follicle Morphogenesis and Hair Tumors in Mice Expressing a Truncated β-Catenin in Skin", Cell, vol. 95, Nov. 1998, pp. 605-614.

Vijajaraghavan et al., "Role for Phosphorylation of Glycogen Synthase Kinase-3α in Bovine Sperm Motility Regulation", Biol. Reprod. vol. 62 Jan. 2000, pp. 1647-1654.

* cited by examiner

COMPOUNDS IN THE TREATMENT OF DEMENTIA RELATED DISEASES, ALZHEIMER'S DISEASE AND CONDITIONS ASSOCIATED WITH GLYCOGEN SYNTHASE KINASE-3

This application is a 371 of PCT/SE02/02371, filed on Dec. 18, 2002, which claims the benefit of the Provisional Application No. 60/344,885, filed on Dec. 21, 2001.

FIELD OF THE INVENTION

The present invention relates to new compounds of formula I, as a free base or salts thereof, to pharmaceutical formulations containing said compounds and to the use of said compounds in therapy. The present invention further relates to processes for the preparation of compounds of formula I and to new intermediates used in the preparation thereof.

BACKGROUND OF THE INVENTION

Glycogen synthase kinase 3 (GSK3) is a serine/threonine protein kinase composed of two isoforms ($\alpha$ and $\beta$), which are encoded by distinct genes but are highly homologous within the catalytic domain. GSK3 is highly expressed in the central and peripheral nervous system. GSK3 phosphorylates several substrates including tau, $\beta$-catenin, glycogen synthase, pyruvate dehydrogenase and elongation initiation factor 2b (eEF2b). Insulin and growth factors activate protein kinase B, which phosphorylates GSK3 on serine 9 the residue and inactivates it.

Alzheimer's Disease (AD) Dementias, and Taupathies.

AD is characterized by cognitive decline, cholinergic dysfunction and neuronal death, neurofibrillary tangles and senile plaques consisting of amyloid-$\beta$ deposits. The sequence of these events in AD is unclear, but believed to be related. Glycogen synthase kinase 3$\beta$ (GSK3$\beta$) or Tau ($\tau$) phosphorylating kinase selectively phosphorylates the microtubule associated protein $\tau$ in neurons at sites that are hyperphosphorylated in AD brains. Hyperphosphorylated protein $\tau$ has lower affinity for microtubules and accumulates as paired helical filaments, which are the main components that constitute neurofibrillary tangles and neuropil threads in AD brains. This results in depolymerization of microtubules, which leads to dying back of axons and neuritic dystrophy. Neurofibrillary tangles are consistently found in diseases such as AD, amyotrophic lateral sclerosis, parkinsonism-dementia complex of Gaum, corticobasal degeneration, dementia pugilistica and head trauma, Down's syndrome, postencephalatic parkinsonism, progressive supranuclear palsy, Niemann-Pick's Disease and Pick's Disease. Addition of amyloid-$\beta$ to primary hippocampal cultures results in hyperphosphorylation of $\tau$ and a paired helical filaments-like state via induction of GSK3$\beta$ activity, followed by disruption of axonal transport and neuronal death (Imahori and Uchida, J. Biochem 121:179-188, 1997). GSK3$\beta$ preferentially labels neurofibrillary tangles and has been shown to be active in pre-tangle neurons in AD brains. GSK3 protein levels are also increased by 50% in brain tissue from AD patients. Furthermore, GSK3$\beta$ phosphorylates pyruvate dehydrogenase, a key enzyme in the glycolytic pathway and prevents the conversion of pyruvate to acetyl-Co-A (Hoshi et al., PNAS 93:2719-2723, 1996). Acetyl-Co-A is critical for the synthesis of acetylcholine, a neurotransmitter with cognitive functions. Thus, GSK3$\beta$ inhibition may have beneficial effects in progression as well as the cognitive deficits associated with Alzheimer's disease and other above-referred to diseases.

Chronic and Acute Neurodegenerative Diseases.

Growth factor mediated activation of the PI3K/Akt pathway has been shown to play a key role in neuronal survival. The activation of this pathway results in GSK3$\beta$ inhibition. Recent studies (Bhat et. al., PNAS 97:11074-11079 (2000)) indicate that GSK3$\beta$ activity is increased in cellular and animal models of neurodegeneration such as cerebral ischemia or after growth factor deprivation. For example, the active site phosphorylation was increased in neurons vulnerable to apoptosis, a type of cell death commonly thought to occur in chronic and acute degenerative diseases such as Alzheimer's Disease, Parkinson's Disease, amyotrophic lateral sclerosis, Huntington's Disease and HIV dementia, ischemic stroke and head trauma. Lithium was neuroprotective in inhibiting apoptosis in cells and in the brain at doses that resulted in the inhibition of GSK3$\beta$. Thus GSK3$\beta$ inhibitors could be useful in attenuating the course of neurodegenerative diseases.

Bipolar Disorders (BD)

Bipolar Disorders are characterised by manic episodes and depressive episodes. Lithium has been used to treat BD based on its mood stabilising effects. The disadvantage of lithium is the narrow therapeutic window and the danger of overdosing that can lead to lithium intoxication. The recent discovery that lithium inhibits GSK3 at therapeutic concentrations has raised the possibility that this enzyme represents a key target of lithium's action in the brain (Stambolic et al., Curr. Biol. 6:1664-1668, 1996; Klein and Melton; PNAS 93:8455-8459, 1996). Inhibition of GSK3$\beta$ may therefore be of therapeutic relevance in the treatment of BD as well as in AD patients that have affective disorders.

Schizophrenia

GSK3 is involved in signal transduction cascades of multiple cellular processes, particularly during neural development. Kozlovsky et al (Am J Psychiatry 2000 May; 157(5):831-3) found that GSK3$\beta$ levels were 41% lower in the schizophrenic patients than in comparison subjects. This study indicates that schizophrenia involves neurodevelopmental pathology and that abnormal GSK3 regulation could play a role in schizophrenia. Furthermore, reduced $\beta$-catenin levels have been reported in patients exhibiting schizophrenia (Cotter et al., Neuroreport 9:1379-1383 (1998)).

Diabetes

Insulin stimulates glycogen synthesis in skeletal muscles via the dephosphorylation and thus activation of glycogen synthase. Under resting conditions, GSK3 phosphorylates and inactivates glycogen synthase via dephosphorylation. GSK3 is also over-expressed in muscles from Type II diabetic patients (Nikoulina et al., Diabetes 2000 February; 49(2):263-71). Inhibition of GSK3 increases the activity of glycogen synthase thereby decreasing glucose levels by its conversion to glycogen. GSK3 inhibition may therefore be of therapeutic relevance in the treatment of Type I and Type II diabetes and diabetic neuropathy.

Hair Loss

GSK3 phosphorylates and degrades $\beta$-catenin. $\beta$-catenin is an effector of the pathway for keratonin synthesis. $\beta$-catenin stabilisation may be lead to increase hair development. Mice expressing a stabilised $\beta$-catenin by mutation of sites phosphorylated by GSK3 undergo a process resembling de novo hair morphogenesis (Gat et al., Cell 1998 Nov. 25;95

(5):605-14)). The new follicles formed sebaceous glands and dermal papilla, normally established only in embryogenesis. Thus GSK3 inhibition may offer treatment for baldness.

Oral Contraceptives

Vijajaraghavan et al. (Biol Reprod 2000 June; 62 (6): 1647-54) reported that GSK3 is high in motile versus immotile sperm. Immunocytochemistry revealed that GSK3 is present in the flagellum and the anterior portion of the sperm head. These data suggest that GSK3 could be a key element underlying motility initiation in the epididymis and regulation of mature sperm function. Inhibitors of GSK3 could be useful as contraceptives for males.

DISCLOSURE OF THE INVENTION

The object of the present invention is to provide compounds having a selective inhibiting effect at GSK3 as well as having a good bioavailability.

Accordingly, the present invention provides a compound of formula I:

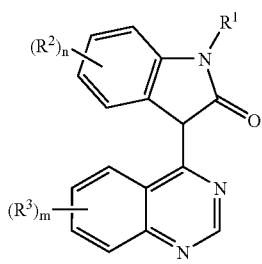

wherein:

$R^1$ is hydrogen;

$R^2$ is carboxy, $C_{2-6}$alkoxycarbonyl, fluoromethyl, difluoromethyl, fluoromethoxy, difluoromethoxy, trifluoromethoxy, or a group $R^4X^1$, wherein $X^1$ is $C_{2-4}$alkanoyl, $CONR^5R^6$, $SO_2NR^7R^8$ or $SO_2R^9$ (wherein $R^5$ and $R^7$ each independently are hydrogen or $C_{1-2}$alkyl and $R^6$, $R^8$ and $R^9$ each independently are $C_{1-4}$alkyl or a bond and wherein $R^4$ is linked to $R^6$, $R^8$ and $R^9$); and $R^4$ is $NR^AR^B$, $OR^A$, $CH(OC_{1-6}alkyl)_2$, or a 7 membered heterocyclic group with one or two heteroatoms selected independently from O, S and N, which heterocyclic group may be saturated or unsaturated and which heterocyclic group may be substituted with one or two substituents selected independently from hydroxy, oxo, halogeno, $C_{1-3}$alkyl, $C_{3-6}$cycloalkyl, $C_{1-3}$alkoxy, $C_{1-3}$alkanoyloxy, $C_{1-3}$alkylOH, $C_{1-3}$alkylphenyl, carbamoyl, $N$—$C_{1-4}$alkylcarbamoyl, $N,N$-di($C_{1-4}$alkyl)carbamoyl, aminosulphonyl, $N$—$C_{1-4}$alkylaminosulphonyl, $N,N$-di($C_{1-4}$alkyl)aminosulphonyl, trifluoromethyl, cyano, amino, nitro and $C_{1-4}$alkoxycarbonyl, and said 7 membered heterocyclic group may optionally be fused with a 5 or 6 membered saturated or unsaturated ring containing atoms selected independently from C, N, O or S, which may be substituted with one or two substituents selected independently from hydroxy, oxo, halogeno, trifluoromethyl, $C_{1-3}$alkyl, $C_{3-6}$cycloalkyl, $C_{1-3}$alkoxy, cyano, amino and nitro; or $R^4$ is a phenyl or a 5 or 6 membered heterocyclic group with one or two heteroatoms selected independently from O, S and N, which heterocyclic group may be saturated or unsaturated and which phenyl or heterocyclic group may be substituted with one or two substituents selected independently from oxo, $C_{3-6}$cycloalkyl, $C_{1-3}$alkylOH, $C_{1-3}$alkylphenyl, carbamoyl, $N$—$C_{1-4}$alkylcarbamoyl, $N,N$-di($C_{1-4}$alkyl)carbamoyl, aminosulphonyl, $N$—$C_{1-4}$alkylaminosulphonyl and $N,N$-di($C_{1-4}$alkyl)aminosulphonyl; or $R^4$ is phenyl or a 5 or 6 membered heterocyclic group with one or two heteroatoms selected independently from O, S and N, which heterocyclic group may be saturated or unsaturated and which phenyl or heterocyclic group may be substituted with one or two substituents selected independently from hydroxy, oxo, halogeno, $C_{1-3}$alkyl, $C_{3-6}$cycloalkyl, $C_{1-3}$alkoxy, $C_{1-3}$alkanoyloxy, $C_{1-3}$alkylOH, $C_{1-3}$alkylphenyl, carbamoyl, $N$—$C_{1-4}$alkylcarbamoyl, $N,N$-di($C_{1-4}$alkyl)carbamoyl, aminosulphonyl, $N$—$C_{1-4}$alkylaminosulphonyl, $N,N$-di($C_{1-4}$alkyl)aminosulphonyl, trifluoromethyl, cyano, amino, nitro and $C_{1-4}$alkoxycarbonyl, and said phenyl or 5 or 6 membered heterocyclic group is fused with a 5 or 6 membered saturated or unsaturated ring containing atoms selected independently from C, N, O or S, which may be substituted with one or two substituents selected independently from hydroxy, oxo, halogeno, trifluoromethyl, $C_{1-3}$alkyl, $C_{3-6}$cycloalky), $C_{1-3}$alkoxy, cyano, amino and nitro; and $R^A$ and $R^B$ are selected independently from hydrogen, $C_{1-6}$alkyl, phenyl and benzyl;

$R^3$ is hydroxy, halogeno, nitro, fluoromethyl, difluoromethyl, trifluoromethyl, fluoromethoxy, difluoromethoxy, trifluoromethoxy, 2,2,2-trifluoroethyl, $C_{1-3}$alkyl, cyano, amino or $R^{10}X^2$, wherein $X^2$ is O, $CH_2$, S, SO, $SO_2$, $NR^{11}CO$, $CONR^{12}$, $SO_2NR^{13}$, $NR^{14}SO_2$ or $NR^{15}$ (wherein $R^{11}$, $R^{12}$, $R^{13}$, $R^{14}$ and $R^{15}$ each independently are hydrogen, $C_{1-3}$alkyl or $C_{1-3}$alkoxy$C_{2-3}$alkyl), or $X^2$ is a direct bond; and $R^{10}$ is selected from one of the following groups:

1) hydrogen or $C_{2-5}$alkyl which may be substituted with one or more groups selected independently from hydroxy, fluoro and amino;

2) $C_{1-5}$alkylX$^3$COR$^{16}$ (wherein $X^3$ is O or $NR^{17}$ (wherein $R^{17}$ is hydrogen, $C_{1-3}$alkyl or $C_{1-3}$alkoxy$C_{2-3}$alkyl) and $R^{16}$ is $C_{1-3}$alkyl, $NR^{18}R^{19}$ or $OR^{20}$ (wherein $R^{18}$, $R^{19}$ and $R^{20}$ each independently are hydrogen, $C_{1-3}$alkyl or $C_{1-3}$alkoxy$C_{2-3}$alkyl));

3) $C_{1-5}$alkylX$^4$R$^{21}$ (wherein $X^4$ is O, S, SO, $SO_2$, OCO, $NR^{22}CO$, $CONR^{23}$, $SO_2NR^{24}$, $NR^{25}SO_2$ or $NR^{26}$ (wherein $R^{22}$, $R^{23}$, $R^{24}$, $R^{25}$ and $R^{26}$ each independently are hydrogen, $C_{1-3}$alkyl or $C_{1-3}$alkoxy$C_{2-3}$alkyl) and $R^{21}$ is hydrogen, $C_{1-3}$alkyl, cyclopentyl, cyclohexyl or a 5 or 6 membered saturated heterocyclic group with one or two heteroatoms selected independently from O, S and N, which $C_{1-3}$alkyl group may be substituted with one or two substituents selected independently from oxo, hydroxy, halogeno and $C_{1-4}$alkoxy and which heterocyclic group may be substituted with one or two substituents selected independently from oxo, hydroxy, halogeno, $C_{1-4}$alkyl, $C_{1-4}$hydroxyalkyl and $C_{1-4}$alkoxy);

4) $C_{1-5}$alkylX$^5$C$_{1-5}$alkylX$^6$R$^{27}$ (wherein $X^5$ and $X^6$ each independently are O, S, SO, $SO_2$, $NR^{28}CO$, $CONR^{29}$, $SO_2NR^{30}$, $NR^{31}SO_2$ or $NR^{32}$ (wherein $R^{28}$, $R^{29}$, $R^{30}$, $R^{31}$ and $R^{32}$ each independently are hydrogen, $C_{1-3}$alkyl or $C_{1-3}$alkoxy$C_{2-3}$alkyl) and $R^{27}$ is hydrogen or $C_{1-3}$alkyl);

5) $C_{1-5}$alkyl$R^{33}$ (wherein $R^{33}$ is a 5 or 6 membered saturated heterocyclic group with one or two heteroatoms selected independently from O, S and N, which $C_{1-5}$alkyl or heterocyclic group may be substituted with one or two substituents selected independently from oxo, hydroxy, halogeno, $C_{1-4}$alkyl, $C_{1-4}$hydroxyalkyl, $C_{2-4}$alkanoyl and $C_{1-4}$alkoxy);

6) $C_{2-5}$alkenyl$R^{33}$ (wherein $R^{33}$ is as defined hereinbefore);

7) $C_{2-5}$alkynyl$R^{33}$ (wherein $R^{33}$ is as defined hereinbefore);

8) $R^{34}$ (wherein $R^{34}$ is a pyridone group, a phenyl group or a 5 or 6 membered aromatic heterocyclic group with 1 to 3 heteroatoms selected independently from O, N and S, which pyridone, phenyl or heterocyclic group may carry up to 5 substituents selected independently from hydroxy, halogeno, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, cyano, $CONR^{35}R^{36}$ and $NR^{37}COR^{38}$ (wherein $R^{35}$, $R^{36}$, $R^{37}$ and $R^{38}$ each independently are hydrogen, $C_{1-4}$alkyl or $C_{1-3}$alkoxy$C_{2-3}$alkyl));

9) $C_{1-5}$alkyl$R^{34}$ (wherein $R^{34}$ is as defined hereinbefore);

10) $C_{2-5}$alkenyl$R^{34}$ (wherein $R^{34}$ is as defined hereinbefore);

11) $C_{2-5}$alkynyl$R^{34}$ (wherein $R^{34}$ is as defined hereinbefore);

12) $C_{1-5}$alkyl$X^7R^{34}$ (wherein $X^7$ is O, S, SO, $SO_2$, $NR^{39}CO$, $CONR^{40}$, $SO_2NR^{41}$, $NR^{42}SO_2$ or $NR^{43}$ (wherein $R^{39}$, $R^{40}$, $R^{41}$, $R^{42}$ and $R^{43}$ each independently are hydrogen, $C_{1-3}$alkyl or $C_{1-3}$alkoxy$C_{2-3}$alkyl) and $R^{34}$ is as defined hereinbefore);

13) $C_{2-5}$alkenyl$X^8R^{34}$ (wherein $X^8$ is O, S, SO, $SO_2$, $NR^{44}CO$, $CONR^{45}$, $SO_2NR^{46}$, $NR^{47}SO_2$ or $NR^{48}$ (wherein $R^{41}$, $R^{45}$, $R^{46}$, $R^{47}$ and $R^{48}$ each independently are hydrogen, $C_{1-3}$alkyl or $C_{1-3}$alkoxy$C_{2-3}$alkyl) and $R^{34}$ is as defined hereinbefore);

14) $C_{2-5}$alkynyl$X^9R^{34}$ (wherein $X^9$ is O, S, SO, $SO_2$, $NR^{49}CO$, $CONR^{50}$, $SO_2NR^{51}$, $NR^{52}SO_2$ or $NR^{53}$ (wherein $R^{49}$, $R^{50}$, $R^{51}$, $R^{52}$ and $R^{53}$ each independently are hydrogen, $C_{1-3}$alkyl or $C_{1-3}$alkoxy$C_{2-3}$alkyl) and $R^{34}$ is as defined hereinbefore); and 15) $C_{1-3}$alkyl$X^{10}C_{1-3}$alkyl$R^{34}$ (wherein $X^{10}$ is O, S, SO, $SO_2$, $NR^{54}CO$, $ONR^{55}$, $SO_2NR^{56}$, $NR^{57}SO_2$ or $NR^{58}$ (wherein $R^{54}$, $R^{55}$, $R^{56}$, $R^{57}$ and $R^{58}$ each independently are hydrogen, $C_{1-3}$alkyl or $C_{1-3}$alkoxy$C_{2-3}$alkyl) and $R^{34}$ is as defined hereinbefore);

16) $R^{33}$ (wherein $R^{33}$ is as defined hereinbefore); and

17) $C_{1-3}$alkyl$X^{10}C_{1-3}$alkyl$R^{33}$ (wherein $X^{10}$ and $R^{33}$ are as defined hereinbefore));

n is 1, 2, 3 or 4;
m is 1, 2, 3 or 4;
as a free base or salts thereof.

One aspect of the invention relates to compounds of formula I, wherein $R^2$ is carboxy, fluoromethyl, difluoromethyl, fluoromethoxy, difluoromethoxy, trifluoromethoxy, or a group $R^4X^1$, wherein $X^1$ is $C_{2-4}$alkanoyl, $CONR^5R^6$, $SO_2NR^7R^8$ or $SO^2R^9$ (wherein $R^5$ and $R^7$ each independently are hydrogen or $C_{1-2}$alkyl and $R^6$, $R^8$ and $R^9$ each independently are $C_{1-4}$alkyl or a bond and wherein $R^4$ is linked to $R^6$, $R^8$ and $R^9$); and $R^4$ is $NR^AR^B$, $OR^A$, $CH(OC_{1-6}alkyl)_2$, or a 7 membered heterocyclic group with one or two heteroatoms selected independently from O, S and N, which heterocyclic group may be saturated or unsaturated and which heterocyclic group may be substituted with one or two substituents selected independently from hydroxy, oxo, halogeno, $C_{1-3}$alkyl, $C_{3-6}$cycloalkyl, $C_{1-3}$alkoxy, $C_{1-3}$alkanoyloxy, $C_{1-3}$alkylOH, $C_{1-3}$alkylphenyl, carbamoyl, N—$C_{1-4}$alkylcarbamoyl, N,N-di($C_{1-4}$alkyl)carbamoyl, aminosulphonyl, N—$C_{1-4}$alkylaminosulphonyl, N,N-di($C_{1-4}$alkyl)aminosulphonyl, trifluoromethyl, cyano, amino, nitro and $C_{1-4}$alkoxycarbonyl, and said 7 membered heterocyclic group may optionally be fused with a 5 or 6 membered saturated or unsaturated ring containing atoms selected independently from C, N, O or S, which may be substituted with one or two substituents selected independently from hydroxy, oxo, halogeno, trifluoromethyl, $C_{1-3}$alkyl, $C_{3-6}$cycloalkyl, $C_{1-3}$alkoxy, cyano, amino and nitro; or $R^4$ is a phenyl or a 5 or 6 membered heterocyclic group with one or two heteroatoms selected independently from O, S and N, which heterocyclic group may be saturated or unsaturated and which phenyl or heterocyclic group may be substituted with one or two substituents selected independently from oxo, $C_{3-6}$cycloalkyl, $C_{1-3}$alkylOH, $C_{1-3}$alkylphenyl, carbamoyl, N—$C_{1-4}$alkylcarbamoyl, N,N-di($C_{1-4}$alkyl)carbamoyl, aminosulphonyl, N—$C_{1-4}$alkylaminosulphonyl and N,N-di($C_{1-4}$alkyl)aminosulphonyl; or $R^4$ is phenyl or a 5 or 6 membered heterocyclic group with one or two heteroatoms selected independently from O, S and N, which heterocyclic group may be saturated or unsaturated and which phenyl or heterocyclic group may be substituted with one or two substituents selected independently from hydroxy, oxo, halogeno, $C_{1-3}$alkyl, $C_{3-6}$cycloalkyl, $C_{1-3}$alkoxy, $C_{1-3}$alkanoyloxy, $C_{1-3}$alkylOH, $C_{1-3}$alkylphenyl, carbamoyl, N—$C_{1-4}$alkylcarbamoyl, N,N-di($C_{1-4}$alkyl)carbamoyl, aminosulphonyl, N—$C_{1-4}$alkylaminosulphonyl, N,N-di($C_{1-4}$alkyl)aminosulphonyl, trifluoromethyl, cyano, amino, nitro and $C_{1-4}$alkoxycarbonyl, and said phenyl or 5 or 6 membered heterocyclic group is fused with a 5 or 6 membered saturated or unsaturated ring containing atoms selected independently from C, N, O or S, which may be substituted with one or two substituents selected independently from hydroxy, oxo, halogeno, trifluoromethyl, $C_{1-3}$alkyl, $C_{3-6}$cycloalkyl, $C_{1-3}$alkoxy, cyano, amino and nitro; and $R^A$ and $R^B$ are selected independently from hydrogen, $C_{1-6}$alkyl, phenyl and benzyl.

In another aspect of the invention $R^2$ is carboxy or $C_{2-6}$alkoxycarbonyl.

In a third aspect of the invention $X^1$ is $CONR^5R^6$ (wherein $R^5$ is hydrogen or $C_{1-2}$alkyl and $R^6$ is $C_{1-4}$alkyl or a bond and wherein $R^4$ is linked to $R^6$).

In yet another aspect of the invention $R^4$ is $NR^AR^B$, $OR^A$, $CH(OC_{1-6}alkyl)_2$, or a 7 membered heterocyclic group with one or two heteroatoms selected independently from O, S and N, which heterocyclic group may be saturated or unsaturated and which heterocyclic group may be substituted with one or two substituents selected independently from hydroxy, oxo, halogeno, $C_{1-3}$alkyl, $C_{3-6}$cycloalkyl, $C_{1-3}$alkoxy, $C_{1-3}$alkanoyloxy, $C_{1-3}$alkylOH, $C_{1-3}$alkylphenyl, carbamoyl, N—$C_{1-4}$alkylcarbamoyl, N,N-di($C_{1-4}$alkyl) carbamoyl, aminosulphonyl, N—$C_{1-4}$alkylaminosulphonyl, N,N-di($C_{1-4}$alkyl)aminosulphonyl, trifluoromethyl, cyano, amino, nitro and $C_{1-4}$alkoxycarbonyl;

$R^A$ and $R^B$ are selected independently from hydrogen, $C_{1-6}$alkyl and phenyl.

In a further aspect of the $R^4$ is phenyl or a 5 or 6 membered heterocyclic group with one or two heteroatoms selected independently from O and N, which heterocyclic group may be saturated or unsaturated and which phenyl or heterocyclic group may be substituted with one or two substituents selected independently from oxo, $C_{3-6}$cycloalkyl, $C_{1-3}$alkylOH, $C_{1-3}$alkylphenyl, carbamoyl, N—$C_{1-4}$ alkylcarbamoyl, N,N-di($C_{1-4}$alkyl)carbamoyl, aminosulphonyl, N—C, alkylaminosulphonyl and N,N-di($C_{1-4}$ alkyl)aminosulphonyl.

In yet another aspect of the invention $R^4$ is phenyl or a 5 or 6 membered heterocyclic group with one or two heteroatoms selected independently from O, S and N, which heterocyclic group may be saturated or unsaturated, and said phenyl or 5 or 6 membered heterocyclic group is fused with a 5 or 6 membered saturated or unsaturated ring containing atoms selected independently from C, N, O or S, which may be substituted with one or two substituents selected independently from hydroxy, oxo, halogeno, trifluoromethyl, $C_{1-3}$alkyl, $C_{3-6}$cycloalkyl, $C_{1-3}$alkoxy, cyano, amino and nitro.

In another aspect of the invention $R^3$ is $R^{10}X^2$, wherein $X^2$ is O; and $R^{10}$ is $C_{1-5}$alkyl$X^4R^{21}$ (wherein $X^4$ is O or $NR^{26}$ (wherein $R^{21}$ and $R^{26}$ independently are hydrogen, $C_{1-3}$alkyl, cyclopentyl or cyclohexyl)); and m is 1 or 2.

One aspect of the present invention relates to compounds having at least one $R^2$ and at least one $R^3$ substituent, wherein $R^3$ represents an ester and $R^2$ is as defined above.

The present invention further relates to compounds of general formula I, wherein the $R^2$ is substituted on position 5 and/or 6 and $R^3$ is substituted on position 6, 7 and/or 8.

In a further aspect of the invention the following compounds are provided:

3-[7-2(-Methoxyethoxy)quinazolin-4-yl]-2-oxo-2,3-dihydro-1H-indole-5-carboxylic acid (2-oxoazepan-3-yl) amide, 2-Hydroxy-3-[7-(2-methoxyethoxy)quinazolin-4-yl]-1H-indole-5-carboxylic acid [3-(methylphenylamino)propyl] amide, 2-Hydroxy-3-[7-(2-methoxyethoxy)quinazolin-4-yl]-1H-indole-5-carboxylic acid [3-(1-hydroxyethyl)phenyl]amide, 2-Hydroxy-3-[7-(2-methoxyethoxy)quinazolin-4-yl]-1H-indole-5-carboxylic acid (4-cyclohexylphenyl)amide, 2-Hydroxy-3-[7-(2-methoxyethoxy)quinazolin-4-yl]-1H-indole-5-carboxylic acid (4,4-diethoxybutyl)amide, 2-Hydroxy-3-[7-(2-methoxyethoxy)quinazolin-4-yl]-1H-indole-5-carboxylic acid (1H-benzoimidazol-2-ylmethyl) amide, 2-Hydroxy-3-[7-(2-methoxyethoxy)quinazolin-4-yl]-1H-indole-5-carboxylic acid [2-(5-methyl-1H-indol-3-yl)ethyl] amide, 2-Hydroxy-3-[7-(2-methoxyethoxy)quinazolin-4-yl]-1H-indole-5-carboxylic acid 4-sulfamoylbenzylamide, 2-Hydroxy-3-[7-(2-methoxyethoxy)quinazolin-4-yl]-1H-indole-5-carboxylic acid (1-benzylpiperidin-4-yl)amide, as a free base or salts thereof.

Listed below are definitions of various terms used in the specification and claims to describe the present invention.

For the avoidance of doubt it is to be understood that where in this specification a group is qualified by 'hereinbefore defined' or 'defined hereinbefore' the said group encompasses the first occurring and broadest definition as well as each and all of the preferred definitions of that group.

For the avoidance of doubt it is to be understood that in this specification '$C_{1-6}$' means a carbon group having 1, 2, 3, 4, 5 or 6 carbon atoms.

In this specification, unless stated otherwise, the term "alkyl" includes both straight and branched chain alkyl groups $C_{1-6}$alkyl may be methyl, ethyl, n-propyl, i-propyl, n-butyl, i-butyl, s-butyl, t-butyl, n-pentyl, i-pentyl, t-pentyl, neo-pentyl, n-hexyl or i-hexyl.

In this specification, unless stated otherwise, the term "$C_{3-6}$cycloalkyl" includes cyclopropyl, cyclobutyl, cyclopentyl and cyclohexyl.

The term "alkoxy" as used herein, unless stated otherwise includes "alkyl"O groups in which "alkyl" is as hereinbefore defined. $C_{1-6}$alkoxy may be methoxy, ethoxy, n-propoxy, i-propoxy, n-butoxy, i-butoxy, s-butoxy, t-butoxy, n-pentyloxy, i-pentyloxy, t-pentyloxy, neo-pentyloxy, n-hexyloxy or i-hexyloxy.

The term "alkanoyl" as used herein, unless otherwise stated includes formyl and alkylC═O groups in which "alkyl" is as defined hereinbefore, for example $C_2$alkanoyl is ethanoyl and refers to $CH_3C$═O, $C_1$alkanoyl is formyl and refers to CHO.

In this specification, unless stated otherwise, the term "alkenyl" includes both straight and branched chain alkenyl groups but references to individual alkenyl groups such as 2-butenyl are specific for the straight chain version only. Unless otherwise stated, the term "alkenyl" advantageously refers to chains with 2 to 5 carbon atoms, preferably 3 to 4 carbon atoms.

In this specification, unless stated otherwise, the term "alkynyl" includes both straight and branched chain alkynyl groups but references to individual alkynyl groups such as 2-butynyl are specific for the straight chain version only. Unless otherwise stated, the term "alkynyl" advantageously refers to chains with 2 to 5 carbon atoms, preferably 3 to 4 carbon atoms.

In this specification, unless stated otherwise, the term "bond" may be a saturated or unsaturated bond.

In this specification, unless stated otherwise, the term "5 or 6 membered heterocyclic group with one or two heteroatoms selected independently from O, S and N, which heterocyclic group may be saturated or unsaturated" and "7 membered heterocyclic group with one or two heteroatoms selected independently from O, S and N, which heterocyclic group may be saturated or unsaturated" includes both heteroaromatic rings and heterocyclic rings that are saturated. Examples of such heterocyclic groups includes, but are not limited to, furyl, isoxazolyl, isothiazolyl, oxa-azepanyl, oxazolyl, pyrazinyl, pyrazolyl, pyridazinyl, pyridyl, pyrimidyl, pyrrolyl, thiazolyl, thienyl, imidazolyl, imidazolidinyl, imidazolinyl, morpholinyl, piperazinyl, piperidyl, piperidonyl, pyrazolidinyl, pyrazolinyl, pyrrolidinyl, pyrrolinyl, tetrahydropyranyl or thiomorpholinyl.

In this specification, unless stated otherwise, the term "5 or 6 membered saturated or unsaturated ring containing atoms selected from C, N, O or S" may be, but are not limited to, furyl, isoxazolyl, isothiazolyl, oxazolyl, pyrazinyl, pyrazolyl, pyridazinyl, pyridyl, pyrimidyl, pyrrolyl, thiazolyl, thienyl, imidazolyl, imidazolidinyl, imidazolinyl, morpholinyl, piperazinyl, piperidyl, piperidonyl, pyrazolidinyl, pyrazolinyl, pyrrolidinyl, pyrrolinyl, tetrahydropyranyl, thiomorpholinyl, phenyl, cyclohexyl or cyclopentyl.

In this specification, unless stated otherwise, the term "5 or 6 membered saturated heterocyclic group with one or two heteroatoms selected independently from O, S and N" may be, but are not limited to, imidazolidinyl, morpholinyl, piperazinyl, piperidinyl, piperidonyl, pyrazolidinyl, pyrazolidinyl, pyrrolidinyl, tetrahydropyranyl or thiomorpholinyl.

In this specification, unless stated otherwise, the term "5 or 6 membered aromatic heterocyclic group with 1 to 3 heteroatoms selected independently from O, N and S" may be, but are not limited to, furyl, imidazolyl, isoxazolyl, isothiazolyl, oxazolyl, pyrazinyl, triazinyl, pyrazolyl, pyridazinyl, pyridyl, pyrimidyl, pyrrolyl, thiazolyl or thienyl.

In this specification, unless stated otherwise, the term halogeno may be fluor, chlorine, bromine or iodine.

For the avoidance of any doubt, it is to be understood that when $X^2$ is, for example, a group of formula $NR^{11}CO$, it is the nitrogen atom be substituted withing the $R^{11}$ group which is attached to the quinazoline ring and the carbonyl (CO) group is attached to $R^{10}$, whereas when $X^2$ is, for example, a group of formula $CONR^{12}$, it is the carbonyl group which is attached to the quinazoline ring and the nitrogen atom be substituted withing the $R^{12}$ group is attached to $R^{10}$. A similar convention applies to the other two atoms $X^2$ linking groups such as $NR^{14}SO_2$ and $SO_2NR^{13}$. When $X^2$ is $NR^{15}$ it is the nitrogen atom be substituted withing the $R^{15}$ group, which is linked to the quinazoline ring and to $R^{10}$. An analogous convention applies to other groups. It is further to be understood that when $X^2$ represents $NR^{15}$ and $R^{15}$ is $C_{1-3}$alkoxy$C_{2-3}$alkyl it is the $C_{2-3}$alkyl moiety, which is linked to the nitrogen atom of $X^2$ and an analogous convention applies to other groups.

For the avoidance of any doubt, it is to be understood that in a compound of formula I when $R^{10}$ is, for example, a group of formula $C_{1-5}$alkyl$X^{10}C_{1-5}$alkyl$R^{34}$, it is the terminal $C_{1-5}$alkyl moiety, which is linked to $X^{10}$, similarly when $R^{10}$ is, for example, a group of formula $C_{2-5}$alkenyl$R^{34}$ it is the $C_{2-5}$alkenyl moiety, which is linked to $X^2$ and an analogous convention applies to other groups.

For the avoidance of any doubt, it is to be understood that when $R^{34}$ carries a $C_{1-4}$aminoalkyl substituent it is the $C_{1-4}$alkyl moiety, which is attached to $R^{34}$ whereas when $R^{34}$ carries a $C_{1-4}$alkylamino substituent it is the amino moiety, which is attached to $R^{39}$ and an analogous convention applies to other groups.

For the avoidance of any doubt when $X^1$ is $C_{2-4}$alkanoyl it is the carbonyl moiety, which is linked to the heteroaromatic oxindole group and it is the alkyl moiety, which is linked to $R^4$ and an analogous convention applies to other groups.

The present invention relates to the use of compounds of formula I as hereinbefore defined as well as to the salts thereof. Salts for use in pharmaceutical compositions will be pharmaceutically acceptable salts, but other salts may be useful in the production of the compounds of formula I and their pharmaceutically acceptable salts.

Both organic and inorganic acids can be employed to form non-toxic pharmaceutically acceptable acid addition salts of the compounds of this invention.

A suitable pharmaceutically acceptable salt of the compounds of the invention is, for example, an acid-addition salt, for example an inorganic or organic acid. In addition, a suitable pharmaceutically acceptable salt of the compounds of the invention is an alkali metal salt, an alkaline earth metal salt or a salt with an organic base.

Some compounds of formula I may have chiral centres and/or geometric isomeric centres (E- and Z-isomers), and it is to be understood that the invention encompasses all such optical, diastereoisomers and geometric isomers.

The invention also relates to any and all tautomeric forms of the compounds of formula I.

Methods of Preparation

Intermediates

The intermediates used in the preparation of a compound of formula I as a free base or salts thereof, may be prepared by any process known to be applicable to the preparation of chemically-related compounds. Such processes include, for example, those illustrated in PCT application WO 97/42187.

Methods of Preparation of End Products

Another object of the invention relates to processes for the preparation of compounds of formula I, Ib and Ic.

Process A describes the preparation of compounds of formula Ib, wherein $R^2$ is calkoxy, comprising of,

A

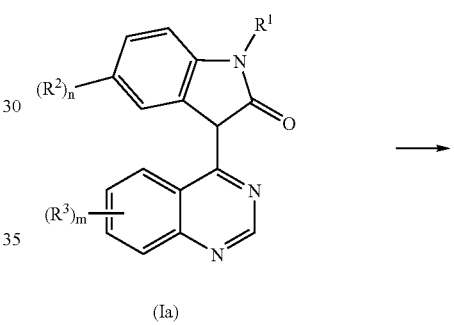

(Ia)

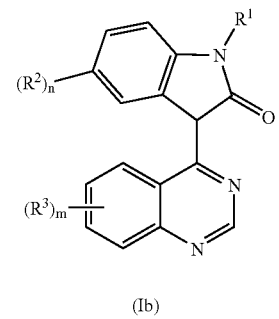

(Ib)

hydrolysis of a compound of formula Ia, wherein $R^2$ is $C_{1-6}$alkoxycarbonyl and $R^1$, $R^3$, m and n are as defined in general formula I, to obtain the compound of formula Ib, wherein $R^2$ is carboxy and $R^1$, $R^3$, m and n are as defined in general formula I, may be carried out under acidic conditions using acids such as $H_2SO_4$, HCl or HBr in a suitable solvent e.g. water, ethanol, methanol or mixtures thereof and the reaction may occur between +20° C. and +100° C. or under basic conditions using bases such as sodium hydroxide or potassium hydroxide in a suitable solvent e.g. water, ethanol, methanol or mixtures thereof and the reaction may occur at a temperature between +20° C. and +100° C.

Process B describes the preparation of compounds of formula Ic, wherein $R^2$ is $R^4X^1$, comprising of

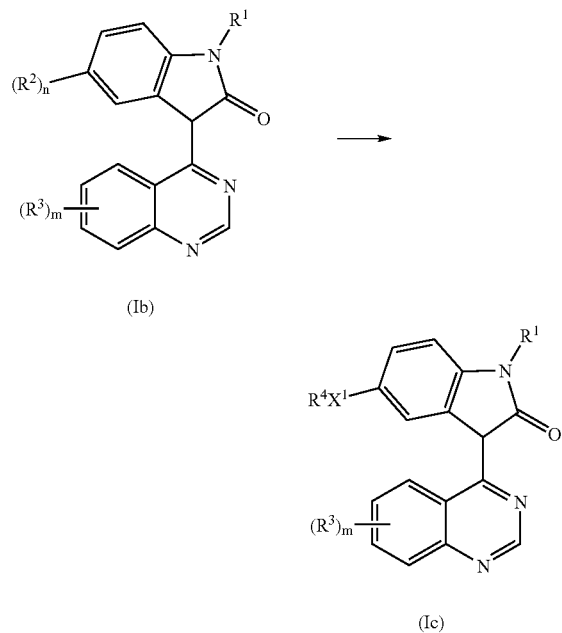

(Ib)

(Ic)

Amidation of a compound of formula Ib, wherein $R^2$ is carboxy and $R^1$, $R^3$, m and n are as defined in general formula I, to obtain a compound of formula Ic, wherein $R^2$ is $R^4X^1$ and $X^1$ is $CONR^5R^6$ and $R^1$, $R^3$, $R^4$, $R^5$, $R^6$, m and n are as defined in general formula I may be performed by activation of a compound of formula Ib, wherein $R^2$ is carboxy, by treating the compound with coupling reagents e.g. 1-[3-(dimethylamino)propyl]-3-ethylcarbodiimide hydrochloride and 1-hydroxybenzotriazole hydrate or hydroxybenzimidazole, 1,3-dicyclohexylcarbodiimide and 1-hydroxybenzotriazole hydrate, 1,1'-carbonyldiimidazole or O-(7-azabenzotriazol-1-yl)-N,N,N',N'-tetramethyluronium hexafluorophosphate, or using an acyl halide reagent e.g. cyanuric chloride, oxalyl chloride, thionyl chloride or bromotrispyrrolidinophosphonium hexafluorophosphate, followed by treatment with the appropriate amine with or without the presence of N,N-dimethylaminopyridine, in a suitable solvent such as N,N-dimethylformamide, tetrahydrofuran, N-methylpyrrolidone, methylene chloride or chloroform at a reaction temperature between 0° C. and +80° C.

Alternatively, compounds of formula I, may be preparared by process C, comprising of

C

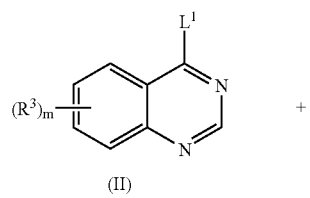

(II)

-continued

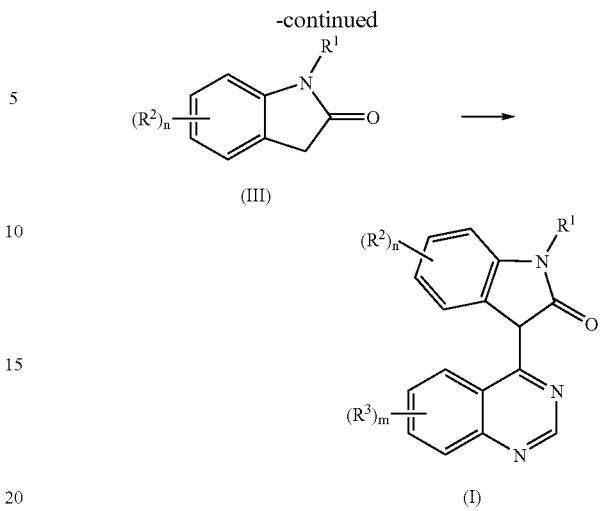

(III)

(I)

reacting a compound of formula II, wherein $L^1$ is a leaving group such as $SCH_3$ or a halogen e.g. chlorine or bromine and $R^3$ and m are as defined in general formula I, with a compound of formula III, wherein $R^1$, $R^2$, and n are as defined in general formula I.

Thus, the reaction of the process may be carried out in an appropriate solvent such as an ether e.g. tetrahydrofuran or 1,4-dioxan, an aromatic hydrocarbon solvent such as toluene, or a dipolar aprotic solvent such as N,N-dimethylformamide, N,N-dimethylacetamide, N-methylpyrrolidin-2-one or dimethylsulphoxide and the reaction is conveniently effected at a temperature in the range of +10 to +150° C., preferably in the range of +20 to +90° C. The reaction is advantageously effected in the presence of a base. Such a base may be an organic amine base such as pyridine, 2,6-lutidine, collidine, 4-dimethylaminopyridine, triethylamine, morpholine, N-methylmorpholine or diazabicyclo [5.4.0]undec-7-ene, tetramethylguanidine, an alkali metal or alkaline earth metal carbonate or hydroxide such as sodium carbonate, potassium carbonate, calcium carbonate, sodium hydroxide or potassium hydroxide. Alternatively, such a base is an alkali metal hydride such as sodium hydride, or an alkali metal or alkaline earth metal amide such as sodium amide, sodium bis(trimethylsilyl)amide, potassium amide or potassium bis(trimethylsilyl)amide. When it is desired to obtain the acid salt, the free base may be treated with an acid, using a conventional procedure.

Intermediates

The present invention further relates to new compounds and the use of these compounds in the preparation of compounds of formula I as defined hereinbefore.

In one aspect of the invention the compound is a compound of formula II,

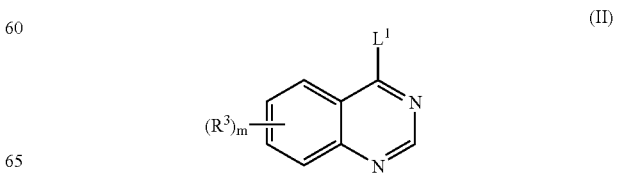

(II)

wherein:

$L^1$ is $SCH_3$;

$R^3$ is $R^{10}X^2$, wherein $X^2$ is O, $CH_2$, S, SO, $SO_2$, $NR^{11}CO$, $CONR^{12}$, $SO_2NR^{13}$, $NR^{14}SO_2$ or $NR^{15}$ (wherein $R^{11}$, $R^{12}$, $R^{13}$, $R^{14}$ and $R^{15}$ each independently are hydrogen, $C_{1-3}$alkyl or $C_{1-3}$alkoxy$C_{2-3}$alkyl), or $X^2$ is a direct bond; and $R^{10}$ is $C_{1-5}$alkyl$X^4R^{21}$ (wherein $X^4$ is O or $NR^{26}$ (wherein $R^{21}$ and $R^{26}$ independently are hydrogen, $C_{1-3}$alkyl, cyclopentyl or cyclohexyl)); and m is 1 or 2.

In one aspect of the invention the compounds 2-Hydroxy-3-[7-(2-methoxyethoxy)quinazolin-4-yl]-1H-indole-5-carboxylic acid, methyl 2-hydroxy-3-[7-(2-methoxyethoxy)quinazolin-4-yl]-1H-indole-5-carboxylate and compounds of formula II are used for the preparation of compounds of formula I.

EXAMPLES

The invention will now be illustrated by the following non-limiting Examples.

Example 1

Methyl 2-hydroxy-3-[7-(2-methoxyethoxy)quinazolin-4-yl]-1H-indole-5-carboxylate

Sodium hydride (58 mg, 1.45 mmol, 60% in oil) was washed with petroleum ether (3×5 mL) and dried in vacuo. The solid was suspended in tetrahydrofuran (3 mL) and methyl 2-oxo-5-indolinecarboxylate (140 mg, 0.73 mmol) in tetrahydrofuran (2 mL) and N-methylpyrrolidinone (2 mL) was added. The reaction mixture was stirred for 30 min at room temperature. A solution of 4-chloro-7-(2-methoxyethoxy)quinazoline (183 mg, 0.77 mmol, described in WO 97/42187) in tetrahydrofuran (2 mL) and N-methylpyrrolidinone (1 mL) was added and the reaction mixture was stirred for 1.5 h at room temperature. The solvent was removed in vacuo and 1 M hydrochloric acid was added. The precipitate formed was filtered off and dried at 40° C. in vacuo over night to give 150 mg (99% yield) of the title compound as an orange solid: MS (AP+) m/z 394.2 ($M^++1$).

Example 2

2-Hydroxy-3-[7-(2-methoxyethoxy)quinazolin-4-yl]-1H-indole-5-carboxylic acid

To a mixture of methyl 2-hydroxy-3-[7-(2-methoxyethoxy)quinazolin-4-yl]-1H-indole-5-carboxylate (5.15 g, 13.1 mmol), methanol (100 mL) and water (50 mL) was added aqueous sodium hydroxide (92 mL, 1 M) and the reaction mixture was stirred at 40° C. over night. Methanol was removed in vacuo and the basic aqueous layer was acidified with 1 M hydrochloric acid and stirred for 30 min. The precipitate formed was filtered off, washed with hydrochloric acid (50 mL, 1 M) and water (2×50 mL) and dried in vacuo at 50° C. over night. The crude product was stirred in methanol at room temperature over night. The solid was filtered off to give 4.23 g (85% yield) of the title compound as an orange solid: MS (AP+) m/z 380.3 ($M^++1$).

Examples 3-11

General Method A

Stock solution A was prepared by dissolving 2-hydroxy-3-[7-(2-methoxyethoxy)-quinazolin-4-yl]-1H-indole-5-carboxylic acid (2.0 g), (3-dimethylaminopropyl)-3-ethylcarbodiimide hydrochloride (2.2 g) and hydroxybenzimidazole (1.54 g) in N-methylpyrrolidinone (160 mL). Stock solution B was prepared by dissolving N,N-dimethylaminopyridine (2.8 g) in N-methylpyrrolidinone (40 mL).

The amidation reaction was performed by adding solution A (8 mL, corresponding to 2-hydroxy-3-[7-(2-methoxyethoxy)-quinazolin-4-yl]-1H-indole-5-carboxylic acid: 100 mg, 0.26 mmol, 1 eq; (3-dimethylaminopropyl)-3-ethylcarbodiimide hydrochloride: 110 mg, 0.51 mmol, 2.2 eq; hydroxybenzimidazole: 77 mg, 0.57 mmol, 2.2 eq) to a reaction vessel containing the desired amine (0.4 mmol, 1.5 eq). Solution B (2 mL, corresponding to N,N-dimethylaminopyridine: 140 mg, 1.14 mmol, 4.4 eq) was added and the resulting solution was stirred at room temperature over night. The solvent was removed in vacuo to give the crude product.

Example 3

3-[7-2(-Methoxyethoxy)quinazolin-4-yl]-2-oxo-2,3-dihydro-1H-indole-5-carboxylic acid (2-oxoazepan-3-yl)amide The reaction was performed as described in method A using (3S)-3-aminoazepan-2-one (50 mg, 0.40 mmol). The crude product was triturated with acetonitrile to give 109 mg (86% yield) of the title compound: MS (AP+) m/z 490.3 ($M^++1$).

Example 4

2-Hydroxy-3-[7-(2-methoxyethoxy)quinazolin-4-yl]-1H-indole-5-carboxylic acid[3-(methylphenylamino)propyl]amide The reaction was performed as described in method A using N-(3-aminopropyl)-N-methylaniline (0.07 mL, 0.395 mmol). The crude product was triturated with ethyl acetate. The solid was decanted and washed with methanol to give 35 mg (26% yield) of the title compound: MS (AP+) m/z 526.3 ($M^++1$).

Example 5

2-Hydroxy-3-[7-(2-methoxyethoxy)quinazolin-4-yl]-1H-indole-5-carboxylic acid [3-(1-hydroxyethyl)phenyl]amide hydrochloride The reaction was performed as described in method A using 3-(1-hydroxyethyl)aniline (55 mg, 0.395 mmol). The crude product was triturated with hydrochloric acid (1 M) to give 71 mg (55% yield) of the title compound: MS (AP+) m/z 499.2 ($M^++1$).

Example 6

2-Hydroxy-3-[7-(2-methoxyethoxy)quinazolin-4-yl]-1H-indole-5-carboxylic acid (1H-benzoimidazol-2-ylmethyl)amide The reaction was performed as described in method A using 2-(aminomethyl)benzimidazole dihydrochloride (88 mg, 0.395 mmol). The crude product was triturated with acetonitrile to give 28 mg (21% yield) of the title compound: MS (AP+) m/z 509.3 ($M^++1$).

Example 7

2-Hydroxy-3-[7-(2-methoxyethoxy)quinazolin-4-yl]-1H-indole-5-carboxylic acid (4-cyclohexylphenyl) amide hydrochloride The reaction was performed as described in method A using 4-cyclohexylaniline (69 mg, 0.395 mmol). The crude product was triturated with hydrochloric acid (1 M), to give 110 mg (79% yield) of the title compound: MS (AP+) m/z 537.3 ($M^+$+1).

Example 8

2-Hydroxy-3-[7-(2-methoxyethoxy)quinazolin-4-yl]-1H-indole-5-carboxylic acid [2-(5-methyl-1H-indol-3-yl)ethyl]amide hydrochloride The reaction was performed as described in method A using 5-methyltryptamine hydrochloride (83 mg, 0.395 mmol). The crude product was triturated with hydrochloric acid (1 M), to give 101 mg (73% yield) of the title compound: MS (AP+) m/z 536.2 ($M^+$+1).

Example 9

2-Hydroxy-3-[7-(2-methoxyethoxy)quinazolin-4-yl]-1H-indole-5-carboxylic acid 4-sulfamoylbenzylamide The reaction was performed as described in method A using 4-(aminomethyl)benzenesulfonamide hydrochloride (0.06 mL, 0.395 mmol). The crude product was triturated with methanol and the solid was re-crystallised from hot methanol to give 72 mg (51% yield) of the title compound: MS (AP+) m/z 548.3 ($M^+$+1).

Example 10

2-Hydroxy-3-[7-(2-methoxyethoxy)quinazolin-4-yl]-1H-indole-5-carboxylic acid (4,4-diethoxybutyl) amide The reaction was performed as described in method A using 4,4-diethoxybutylamine (0.07 mL, 0.395 mmol). The crude product was washed with acetone and the solid was washed with hot methanol to give 10 mg (7.4% yield) of the title compound: MS (AP+) m/z 523.3 ($M^+$+1).

Example 11

2-Hydroxy-3-[7-(2-methoxyethoxy)quinazolin-4-yl]-1H-indole-5-carboxylic acid (1-benzylpiperidin-4-yl)amide hydrochloride The reaction was performed as described in method A using benzyl-4-piperidylamine (0.08 mL, 0.395 mmol). The crude product was triturated with acetone. The formed solid was stirred in hydrochloric acid (1 M), filtered and dried in vacuo to give 39 mg (27% yield) of the title compound: MS (AP+) m/z 552.4 ($M^+$+1).

Pharmaceutical Compositions

According to one aspect of the present invention there is provided a pharmaceutical composition comprising a compound of formula I, as a free base or salts thereof, for use in prevention and/or treatment of dementia related diseases, Alzheimer's Disease and conditions associated with glycogen synthase kinase-3 and other conditions listed below.

The composition may be in a form suitable for oral administration, for example as a tablet, pill, syrup, powder, granule or capsule, for parenteral injection (including intravenous, subcutaneous, intramuscular, intravascular or infusion) as a sterile solution, suspension or emulsion, for topical administration as an ointment, patch or cream or for rectal administration as a suppository.

In general the above compositions may be prepared in a conventional manner using pharmaceutically carriers or diluents.

Suitable daily doses of the compounds of formula I in the treatment of a mammal, including man, are approximately 0.01 to 250 mg/kg bodyweight at peroral administration and about 0.001 to 250 mg/kg bodyweight at parenteral administration. The typical daily dose of the active ingredients varies within a wide range and will depend on various factors such as the relevant indication, the route of administration, the age, weight and sex of the patient and may be determined by a physician.

Medical Use

Surprisingly, it has been found that the compounds defined in the present invention, as a free base or salts thereof, are useful in therapy. The compounds of the present invention are well suited for inhibiting glycogen synthase kinase-3 (GSK3). Accordingly, the compounds of the present invention are expected to be useful in the prevention and/or treatment of conditions associated with glycogen synthase kinase-3 activity, i.e. the compounds may be used to produce an inhibitory effect of GSK3 in mammals, including man, in need of such prevention and/or treatment.

GSK3 is highly expressed in the central and peripheral nervous system and in other tissues. Thus, it is expected that compounds of the invention are well suited for the prevention and/or treatment of conditions associated with glycogen synthase kinase-3 in the central and peripheral nervous system. In particular, the compounds of the invention are expected to be suitable in the manufacture of a medicament for the prevention and/or treatment of dementia related diseases and Alzheimer's Disease.

The dementia related diseases are selected from the group consisting of Frontotemporal dementia Parkinson's Type, Parkinson dementia complex of Guam, HIV dementia, diseases with associated neurofibrillar tangle pathologies, predemented states, vascular dementia, dementia with Lewy bodies, Frontotemporal dementia and dementia pugilistica.

The compounds of the invention are also expected to be suitable in the manufacture of a medicament for the prevention and/or treatment of amyotrophic lateral sclerosis, corticobasal degeneration, Down syndrome, Huntington's Disease, Parkinson's Disease, postencephelatic parkinsonism, progressive supranuclear palsy, Pick's Disease, Niemann-Pick's Disease, stroke, head trauma and other chronic neurodegenerative diseases, Bipolar Disease, affective disorders, depression, schizophrenia, cognitive disorders, hair loss and contraceptive medication.

The compounds of the invention are further expected to be suitable in the manufacture of a medicament for the prevention and/or treatment of Mild Cognitive Impairment, Age-Associated Memory Impairment, Age-Related Cognitive Decline, Cognitive Impairement No Dementia, mild cognitive decline, mild neurocognitive decline, Late-Life Forgetfulness, memory impairment and cognitive impairment and androgenetic alopecia.

The present invention relates also to the use of a compound of formula I as defined hereinbefore, in the manufacture of a medicament for the prevention and/or treatment of conditions associated with glycogen synthase kinase-3.

In the context of the present specification, the term "therapy" also includes "prevention" unless there are specific indications to the contrary. The terms "therapeutic" and "therapeutically" should be construed accordingly.

The invention also provides for a method of prevention and/or treatment of dementia related diseases, Alzheimer's Disease and conditions associated with glycogen synthase kinase-3 and other conditions listed above comprising administrering to a mammal, including man, in need of such prevention and/or treatment a therapeutically effective amount of a compound of formula I, as hereinbefore defined.

Non-Medical Use

In addition to their use in therapeutic medicine, the compounds of formula I as a free base or salts thereof, are also useful as pharmacological tools in the development and standardisation of in vitro and in vivo test systems for the evaluation of the effects of inhibitors of GSK3 related activity in laboratory animals such as cats, dogs, rabbits, monkeys, rats and mice, as part of the search for new therapeutics agents.

Pharmacology

Determination of ATP Competition in Scintillation Proximity GSK3β Assay.

GSK3β Scintillation Proximity Assay.

The competition experiments were carried out in duplicate with 10 different concentrations of the inhibitors in clear-bottom microtiter plates (Wallac, Finland). A biotinylated peptide substrate, Biotin-Ala-Ala-Glu-Glu-Leu-Asp-Ser-Arg-Ala-Gly-Ser($PO_3H_2$)-Pro-Gln-Leu (AstraZeneca, Lund), was added at a final concentration of 1 μM in an assay buffer containing 1 mU recombinant human GSK3β (Dundee University, UK), 12 mM morpholinepropanesulfonic acid (MOPS), pH 7.0, 0.3 mM EDTA, 0.01% β-mercaptorethanol, 0.004% Brij 35 (a natural detergent), 0.5% glycerol and 0.5 μ g BSA/25 μl. The reaction was initiated by the addition of 0.04 μCi [γ-$^{33}$P]ATP (Amersham, UK) and unlabelled ATP at a final concentration of 1 μM and assay volume of 25 μl. After incubation for 20 minutes at room temperature, each reaction was terminated by the addition of 25 μl stop solution containing 5 mM EDTA, 50 μM ATP, 0.1% Triton X-100 and 0.25 mg streptavidin coated Scintillation Proximity Assay (SPA) beads (Amersham, UK). After 6 hours the radioactivity was determined in a liquid scintillation counter (1450 MicroBeta Trilux, Wallac). The inhibition curves were analysed by non-linear regression using GraphPad Prism, USA. The $K_m$ value of ATP for GSK3β, used to calculate the inhibition constants ($K_i$) of the various compounds, was 20 μM.

The following abbreviations have been used:
ATP Adenosine Triphophatase
BSA Bovin Serum Albumin
EDTA Ethylenediaminetetraacetic acid
GSK3 Glycogen synthase kinase 3
MOPS Morpholinepropanesulfonic acid
SPA Scintillation Proximity Assay Results Typical $K_i$ values for the compounds of the present invention are in the range of about 0.001 to about 10,000 nM. Other values for $K_i$ are in the range of about 0.001 to about 1000 nM. Further values for $K_i$ are in the range of about 0.001 nM to about 300 nM.

The invention claimed is:

1. A compound which is
   3-[7-2(-Methoxyethoxy) quinazolin-4-yl]-2-oxo-2,3-dihydro-1H-indole-5-carboxylic acid (2-oxoazepan-3-yl) amide,
   2-Hydroxy-3-[7-(2-methoxyethoxy)quinazolin-4-yl]-1H-indole-5-carboxylic acid [3-(methylphenylamino)propyl]amide,
   2-Hydroxy-3-[7-(2-methoxyethoxy)quinazolin-4-yl]-1H-indole-5-carboxylic acid [3-(1-hydroxyethyl)phenyl] amide,
   2-Hydroxy-3-[7-(2-methoxyethoxy)quinazolin-4-yl]-1H-indole-5-carboxylic acid (4-cyclohexylphenyl)amide,
   2-Hydroxy-3-[7-(2-methoxyethoxy)quinazolin-4-yl]-1H-indole-5-carboxylic acid (4,4-diethoxybutyl)amide,
   2-Hydroxy-3-[7-(2-methoxyethoxy)quinazolin-4-yl]-1H-indole-5-carboxylic acid (1H-benzoimidazol-2-ylmethyl)amide,
   2-Hydroxy-3-[7-(2-methoxyethoxy)quinazolin-4-yl]-1H-indole-5-carboxylic acid [2-(5-methyl-1H-indol-3-yl)ethyl]amide,
   2-Hydroxy-3-[7-(2-methoxyethoxy)quinazolin-4-yl]-1H-indole-5-carboxylic acid 4-sulfamoylbenzylamide or
   2-Hydroxy-3-[7-(2-methoxyethoxy)quinazolin-4-yl]-1H-indole-5-carboxylic acid (1-benzylpiperidin-4-yl) amide, as a free base or a salt thereof.

* * * * *